Figure 1:
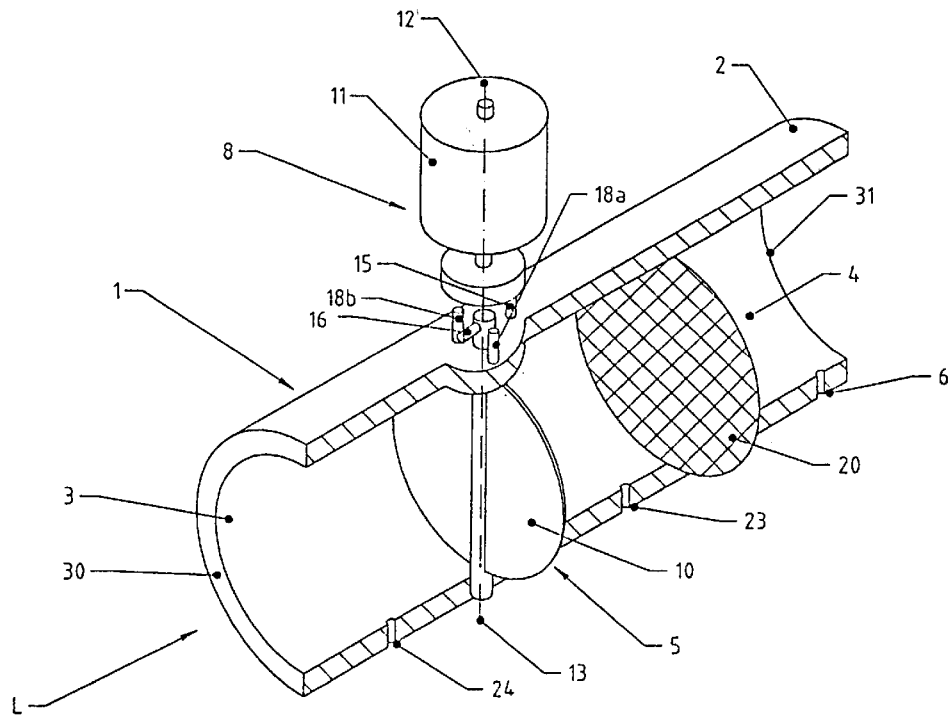

United States Patent [19]
Schiller

[11] Patent Number: 5,868,681
[45] Date of Patent: Feb. 9, 1999

[54] DEVICE AND A METHOD FOR MEASURING THE RESISTANCE OF THE RESPIRATORY TRACT

[75] Inventor: Alfred Schiller, Baar, Switzerland

[73] Assignee: Schiller AG, Baar, Switzerland

[21] Appl. No.: 921,662

[22] Filed: Sep. 2, 1997

[30] Foreign Application Priority Data

Sep. 13, 1996 [CH] Switzerland ............... 2247/96
Oct. 24, 1996 [CH] Switzerland ............... 2608/96

[51] Int. Cl.[6] ...................................... A61B 5/08
[52] U.S. Cl. ................ 600/533; 600/538; 600/540; 600/539
[58] Field of Search .................... 600/533, 538, 600/539, 540, 541, 542

[56] References Cited

U.S. PATENT DOCUMENTS

| | | |
|---|---|---|
| 4,059,847 | 11/1977 | Phillips et al. . |
| 4,197,859 | 4/1980 | Prestele ............................ 600/533 |
| 4,220,161 | 9/1980 | Berlin et al. ..................... 600/533 |
| 4,330,017 | 5/1982 | Satoh et al. . |
| 5,170,011 | 12/1992 | Martucci . |
| 5,233,998 | 8/1993 | Chowienczyk et al. ......... 600/538 |
| 5,356,681 | 10/1994 | Ichikawa et al. . |
| 5,507,993 | 4/1996 | Fortuin et al. . |
| 5,570,711 | 11/1996 | Walsh . |
| 5,621,070 | 4/1997 | Howard, Jr. . |

FOREIGN PATENT DOCUMENTS

| | | |
|---|---|---|
| 0 419 113 A1 | 3/1991 | European Pat. Off. . |
| 36 08 566 A1 | 9/1987 | Germany . |

*Primary Examiner*—Robert L. Nasser
*Assistant Examiner*—Michael Astorino
*Attorney, Agent, or Firm*—Shoemaker and Mattare, Ltd.

[57] ABSTRACT

A device for measuring the resistance of the respiratory tract with the interrupter method consists essentially of a housing (2) which comprises an air passage (3), and of a closing arrangement (5) for temporarily closing the air passage (3). The closing arrangement (5) may be operated via drive means (8). The drive means (8) are arranged and/or designed such that they can be accelerated in a load-free manner from a rest position (R) into an effectual condition (W). In the effectual condition (W) the drive means (8) engages with the closing arrangement and move the latter from a home position (A) into a closing position (V). With this, it is essential that at the point in time of the coming into engagement of the drive means (8) and the closing arrangement (5), the drive means has a certain energy content.

8 Claims, 6 Drawing Sheets

DEVICE AND A METHOD FOR MEASURING THE RESISTANCE OF THE RESPIRATORY TRACT

The invention relates to a device and a method for measuring the resistance of the respiratory tract according to the preamble of the independent claims.

For early recognition of diseases of the respiratory tracts of persons it is known to determine the flow of the exhaled breathing air. Additional possibilities for diagnosis result when the internal resistance of the respiratory tracts is measured. For such measurements so-called interrupter or shutter measuring methods are known. With these methods the test person exhales the breathing air through an air passage in a measuring apparatus with an inlet and an outlet opening. In a first step the flow of the exhaled breathing air through the passage is measured. In a second step the pressure which builds up in the inside of the respiratory tract is measured. For this the passage in the measuring apparatus is briefly closed so that in the respiratory tract, and in the part of the measuring apparatus on the mouth side there builds up a pressure which corresponds to the internal pressure in the respiratory tract. The closing of the passage is effected within a short period of time, for example within 30 to 100 milliseconds. The knowledge of the flow and the built up pressure allows the determination of the internal resistance of the respiratory tract. The resistance is formed by the quotient of the internal pressure of the respiratory tract and the flow of the exhaled breathing air. From the measured flow and the evaluated pressure, by these means, the internal resistance of the respiratory tract may be determined.

The air passage of the measuring apparatus may be repeatedly closed also in intervals during an exhaling procedure. In this way a profile of the resistance of the respiratory tract dependent on the content of the lungs may be produced.

From EP 419 113 A1 there is for example known a device for measuring the resistance of the respiratory tract in which a hole in a housing may be temporarily closed by an elliptical shutter. A similar measuring principle is known from DE OS 24 13 960 or from DE 35 17 786 A1.

The passage of the measuring apparatus at the same time must be closed within a very short time, preferably in the region of a few milliseconds. From this there results high values of acceleration for the shutter which necessitates a large torque for the drive. Accordingly, with the known devices relatively powerful and thus large and expensive drive motors are necessary. This makes the measuring apparatus more expensive, increases the electricity consumption and leads to large apparatus. With the known devices there also arises problems with cleaning the measuring device. Since the drive member and the shutter are rigidly connected to one another, the motor is difficult to separate from the remaining part of the device. The measuring device thus cannot easily be rinsed or disinfected. Neither can disposable components be used. The cleaning and the use of sterile components are however imperative in this field of application.

It is therefore the object of the present invention to avoid the disadvantages of that which is known and in particular to provide a device for measuring the resistance of the respiratory tract which can be economically, simply and compactly manufactured, which ensures the shortest of closing and opening times and moreover permits an simple exchange or cleaning of the flow sensor. In particular, a device is also to be provided which at the same time can be reliably operated with smaller drive motors. A further object of the invention lies in providing a method for closing the air passage of a device for measuring the resistance of the respiratory tract, this able to be carried out with motors which are more compact and less powerful compared to those of conventional devices. According to the invention these objects are achieved with a device and a method with those features of the characterising part of the independent patent claims.

A device for measuring the resistance of the respiratory tract consists essentially of a housing with an air passage with an inlet and outlet opening. When measuring the resistance of the respiratory tract, the test person exhales the breathing air through the air passage. The device contains means for measuring the flow of the exhaled breathing air through the opening as well as a valve for temporarily closing the air passage. The means for measuring the flow may for example consist of a flow resistance arranged in the air passage with a pressure measuring arrangement in front of and behind the resistance. With this, by way of the reduction in pressure at the resistance, the flow of the exhaled breathing air is determined.

The housing further comprises a measuring arrangement for measuring the pressure between the inlet opening and the valve.

The valve can be moved, by way of drive means, between a home position and a closing position. In the home position the air passage is essentially non-closed, in the closing position the air passage is sealingly closed by the valve, so that a pressure may build up between the valve and the inlet opening of the device.

The valve and the drive means are furthermore connectable to one another via a coupling arrangement so that the air passage can be closed on operation of the drive means. The drive means is so designed or arranged that it can be accelerated or moved from a resting position into an effectual condition in a load-free manner. In the effectual condition the drive means have achieved a predetermined minimum energy content. This content may be defined by a certain effectual speed or rotational speed, or also potential energy (spring tension). Load free in this context is to be understood in that the drive means starts the closing device without external load. This means that at the point in time of starting, there exists no coupling between the drive means and the valve. Only in the effectual condition does the drive means engage with the valve.

At the same time it is essential that the drive means, at the point in time at which it becomes connected to the valve, already has a relatively high energy content (rotational energy, movement energy, spring tension). The energy content (for example rotational energy) is built up, whilst the valve still remains closed. This arrangement permits the use of relatively small or less powerful drive means, for example small electrical motors. The valve stands still whilst the drive means is accelerated from a resting position to a certain speed or proceeds to a condition. Only after reaching this speed or the condition (and the energy stored with this) does the drive means come into engagement with the valve.

With the sum of kinetic and/or rotational energy and the driving energy of the drive means, the valve is accelerated and in the shortest of times is moved from the home position to the closing position (or from the closing position again back to the home position). Because the drive means and the valve are not rigidly connected to one another, the drive means is also swiftly and simply released from the remainder of the measuring device. In this manner the housing with the air passage and the valve may be simply cleaned, or designed as a disposable component.

In a particularly advantageous embodiment example the passage of the housing is formed round and the valve consists of a rotatably mounted shutter. It is particularly favourable when the drive means consists of an electrical motor, whose axis is concentrically arranged with the rotational axis of the shutter.

The motor may be provided with a driving pin which can be brought into engagement with an eccentric stop face of the shutter. On operating the drive means, the motor rotates freely so long until the driving pin hits the stop face of the shutter. At this point in time the shutter moves away from its home position. With this it is advantageous that the motor, at the point in time when driving pin hits the stop face, has already built up a certain rotational energy which can be transferred to the shutter. Afterwards the shutter is rotated into the desired new position by the motor. Preferably this position is defined by a stop in the inside of the air passage of the measuring device. In the present embodiment example in which the shutter is moved from a home position into a closing position (and back), there are preferably arranged two stops, i.e. a stop for each position. It is however also conceivable to apply an elliptical shutter in a round opening. In this manner the stop defining the closing position may be omitted.

Of course a multitude of other couplings between the drive means and the valve are possible. Conceivable for example would be centrifugal force couplings, gearwheels which are only provided with teeth over a certain angular region or springs (spiral or helical) which may be brought into an effectual condition with a desired potential energy. Furthermore it is also conceivable to use linear instead of rotating drive means.

The method according to the invention for temporarily closing and opening the air passage of a device for measuring the resistance of the respiratory tract is characterised essentially by the fact that in a first step, drive means, for moving a valve in a load-free manner from a rest position into an effectual condition, are accelerated or moved. In the effectual condition the drive means comprises kinetic energy and/or rotational energy or potential energy having a certain value. Only in the effectual condition is the drive means brought into engagement with a valve for closing the air passage. Subsequently the valve is moved by the drive means from a home position into a closing position.

The basic concept of the invention thus lies essentially in the fact that on the one hand the drive means is not rigidly connected to the valve, and that on the other hand the drive means may build up a certain energy, before it at all comes into engagement with the mass to be accelerated.

Instead of a rotatably mounted shutter, other valve with different constructions are also conceivable. Thus for example rectangular or laminar constructed valve may also be employed. Laminar valve are noted for a reduced space requirement in comparison to a shutter designed as one piece.

Figure 2:
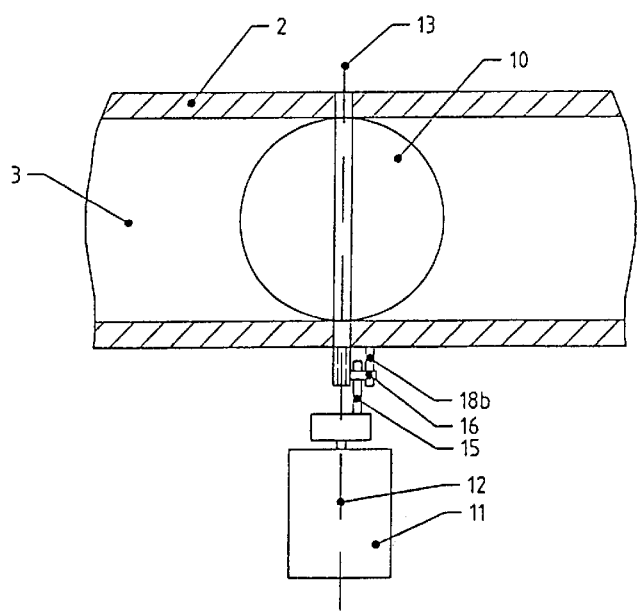
Figure 3A:
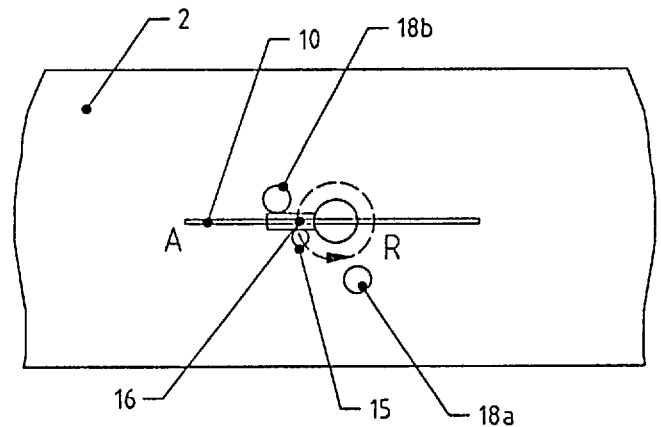
Figure 3B:
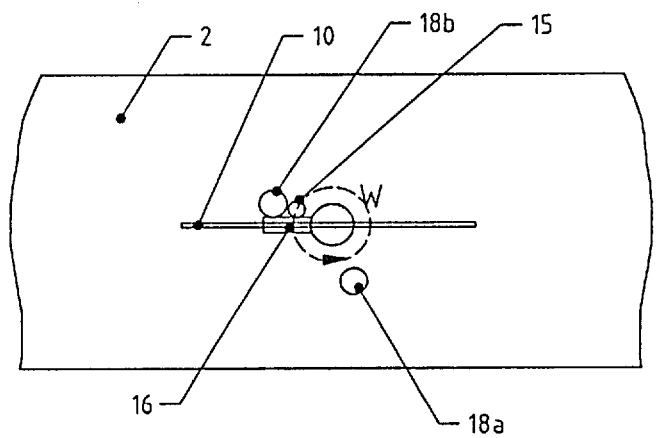
Figure 3C:
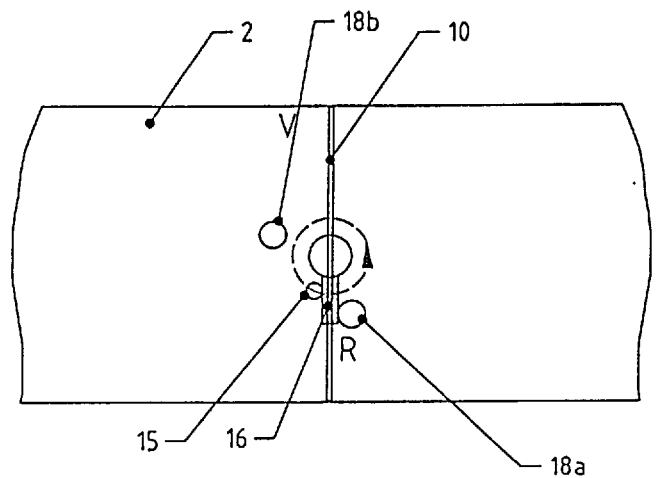
Figure 3D:
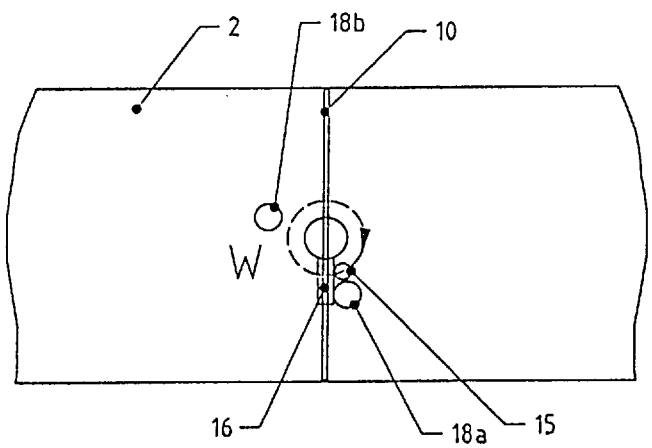
Figure 3E:
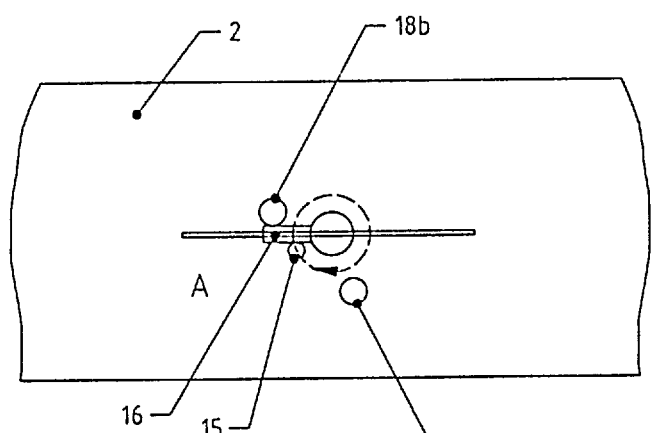
Figure 4:
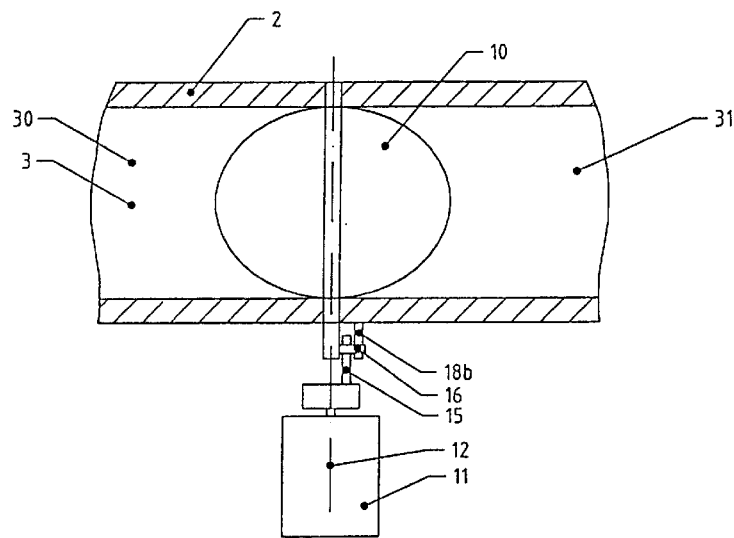
Figures 5A, 5B:
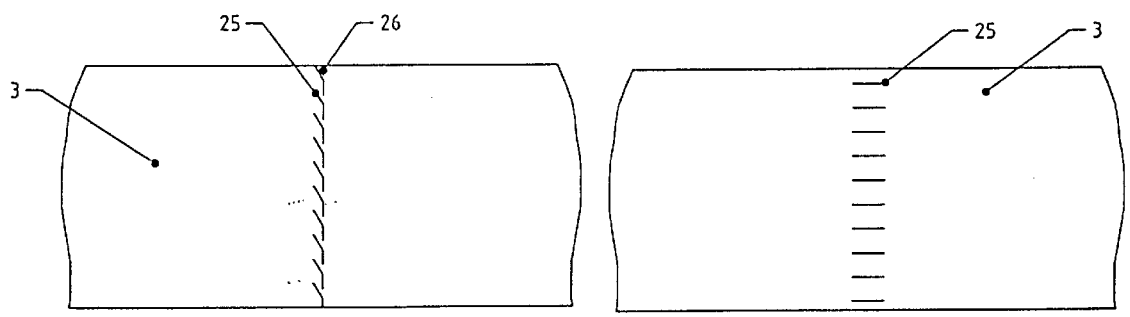
Figure 6:
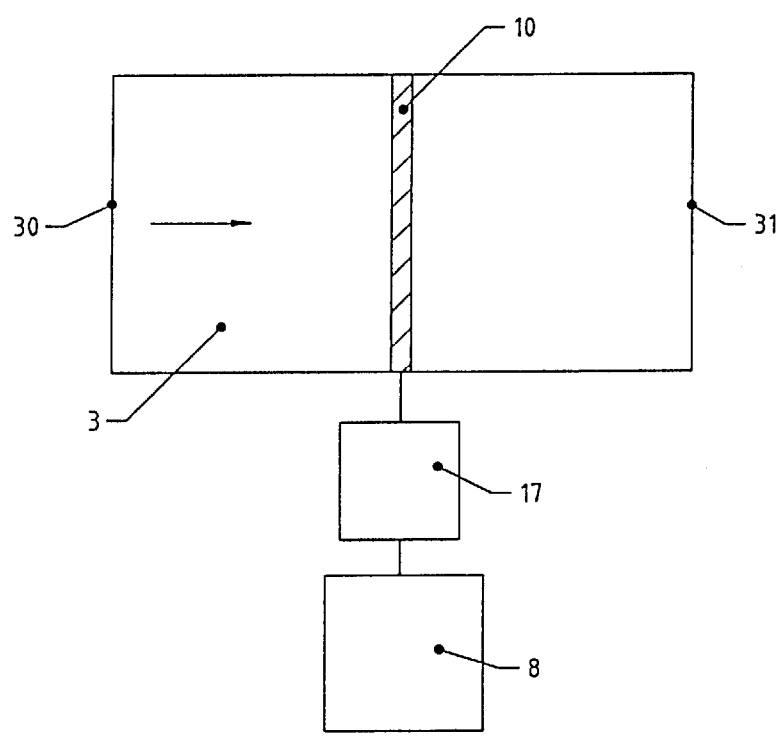

The invention is hereinafter described in more detail by way of the drawings, and in embodiment examples. There are shown:

FIG. 1 a perspective representation of a cut-open device according to the invention, FIG. 2 a cross section through the device according to the invention, FIGS. 3a to 3e a plan view of the device according to the invention in various working positions, FIG. 4 a cross section of a further embodiment example of a device according to the invention, FIGS. 5a and 5b a further embodiment example of a closing arrangement of a device according to the invention in an opened condition (FIG. 5b) and in a closed position (FIG. 5a), and FIG. 6 a schematic representation of the device according to the invention, in a general form.

FIG. 1 shows a schematic perspective representation of a cut-open measuring device 1 according to the invention. The measuring device 1 consists essentially of a housing 2 comprising an air passage 3 having an inlet opening 30 and an outlet opening 31. For determining the resistance of the respiratory tract of a test person, this test person pushes the breathing air L through the inlet opening 30 of the measuring device 1. The device 1 further comprises measuring means 4 for measuring the flow of the exhaled breathing air. The measuring means 4 consists essentially of a flow resistance 20, for example in the form of a gauze and of two pressure measuring arrangements 6, 23 which measure the pressure on both sides of the flow resistance 20.

For determining the resistance of the repiratory tract additionally to the flow of exhaled breathing air L, the pressure which builds up in the inside of the respirartory tract must also be measured. For this the so-called interrupter method is applied. The air passage 3 is temporarily closed by way of a valve 5. FIG. 1 shows the measuring device 1 in the closed condition. The air passage is closed during 30 to 100 milliseconds, typically 70 milliseconds. When the valve 5 has occluded the passage 3, by way of a pressure gauge 24, the pressure which builds up in the inside of the measuring device 1 is measured. This pressure corresponds to the inner pressure in the respiratory tract.

In the embodiment example according to FIG. 1, the valve 5 consists of a shutter 10 which can be moved via a drive means 8 between a home position A (FIG. 3a) in which the air passage 3 is not closed, and a closing position V (FIG. 3c). The drive means 8 consist of an electrical motor 11 which is connectable to the shutter 10. On the inner or outer side of the air passage 3 there are furthermore provided two stops 18a, 18b which define the two end positions of the shutter 10 (home position A, closing position V). The shutter 10 is thus moved by way of the drive means 8 between the two positions defined by the stops 18a, 18b. Generally the movement lasts a few milliseconds.

The shutter 10 is not rigidly connected to the motor 11. This permits a swift separation of the motor 11 with respect to the whole drive means 8 and the housing 2 of the measuring device 1. This permits a simple cleaning of the housing or the application of disposable housings.

The shutter 10 is rotatably mounted about an axis 13 in the housing 2. The axis 12 of the motor 11 is coaxially arranged with the rotational axis 13 of the shutter 10. The motor comprises a driving pin 15 which may be brought into engagement with a stop face 16 of the shutter. For moving the shutter 10 from the home position A into the closed position V (or back), the motor 11 is operated. Because the motor 11 is not rigidly connected to the shutter 10, in the first step it accelerates largely in a load-free manner, whilst the shutter 10 remains in its position. In this context load-free is to be understood in that the motor only runs against its own inertia and not with the external loading of the shutter 10. After the motor has carried out a rotation through approximately 360° (see FIGS. 3a to 3e) the driving pin 15 comes into engagement with the stop face 16. In this way the shutter 10 is brought from the home position A into the closing position V (or vice versa). The stops 18a, 18b define the end positions of this movement.

Because the motor, at the point in time when the driving pin 15 engages with the stop face 16, has already built up rotational energy, the shutter 10 is accelerated very quickly. This permits the application of comparatively less powerful motors without having to accept long closing or opening times.

FIG. 2 shows a cross section through a device according to the invention in which the shutter 10 stands in the home position A in which the passage 3 is not closed. The home position A is defined by the stop 18b in the inside of the air passage 3. FIG. 2 shows how the motor 11 and the shutter 10 are arranged coaxially with regard to their rotational axes 12, 13. The shutter 10 and the motor 11 are arranged so that they are freely rotatably mounted about a given circumferential angle. At the latest, after a rotation of 360 degrees, the motor 11 engages with the stop face 16 of the shutter 10 via the driving pin 15.

FIGS. 3a to 3e illustrate the opening and closing procedure.

FIG. 3a schematically shows the plan view of the device according to the invention in which the shutter 10 is in the home position A. In this condition the flow of the exhaled breathing air L is measured with the device. The position of the shutter 10 is defined by the stop 18b. According to FIG. 3a the shutter 10 is pressed on the stop 18b by the driving pin 15. The motor 11 is located in a rest position R. This is not compelling but helps in exactly defining the home position A of the shutter 10 and in keeping the shutter 10 in this position until operation of the motor. When the air passage 3 is to be closed with the shutter 10, according to the projection in FIG. 3a, the motor 11 is set in an anticlockwise motion. In this way the motor may be freely accelerated over an angular range of approximately 360 degrees until it comes into engagement with the stop face 16 in an effectual condition W (see FIG. 3b). At this point in time the motor has already built up sufficient rotational energy in order to swiftly accelerate the shutter 10.

FIG. 3c shows the device 1 according to the invention in which the shutter 10 is located in the closing position V. The shutter 10 rests on the stop 18a. The driving pin 15 is still in engagement with the stop face 16. In this way the shutter 10 is secured in the closing position V in an exactly defined manner.

For returning the shutter 10 into the home position A the motor 11 is operated in the reverse direction (in the elevation according to FIG. 3d in the anticlockwise direction). The motor 11 can then again be accelerated load-free about a circumferential angle of approximately 360 degrees. After a rotation of 360 degrees the driving pin 15 in an effectual condition W engages with the stop face 16 of the shutter 10. In this way the shutter is brought into the home position A (see FIG. 3e) and is pressed against the first stop 18.

FIG. 3e corresponds essentially to FIG. 3a, wherein in FIG. 3e it becomes clear that the driving pin 15 generally presses the shutter 10 against the stop 18b, since the movement of the shutter 10 is only halted by way of the stop 18b.

FIG. 4 shows an alternative embodiment example of a device according to the invention in which the shutter 10 is formed elliptically. With such a design the stop which defines the closing position V becomes unnecessary. The elliptical shutter 10 rests on the inner wall of the air passage 3 by which means the closing position V is defined.

FIGS. 5a and 5b show a further alternative embodiment example of a valve. The closing arrangement in this case consists of a multitude of lamellae 25 which are each rotatable about a rotational axis 26. FIG. 5a shows the lamellae 25 in a closing position in which the passage 3 is closed. FIG. 5b shows the opened lamellae 25 which permit a discharge of the breathing air through the passage 3. This arrangement is particularly noted by its reduced space requirement. The mass of the parts to be moved furthermore lie in the vicinity of the rotational axis of the individual lamellae, by which means there results a low moment of inertia and a small energy effort for moving the lamella arrangement. The individual lamellae 25 are so connected to one another that they may be simultaneously moved by a drive means. As a drive means, drives which accelerate load-free as previously described are employed.

FIG. 6 schematically shows the construction of a device according to the invention. The valve 10 is connectable to the drive means by way of a coupling arrangement 17.

The coupling arrangement in addition to the previously described possibility (driving pin), may also consist of a centrifugal force coupling, specifically formed gearwheels or other known coupling devices.

I claim:

1. A device for measuring the resistance of the respiratory tract, comprising a housing having an air passage with an inlet opening and an outlet opening formed therein, means for measuring an air flow through said air passage, a valve for temporarily interrupting said flow by way of closing said air passage, a measuring means for measuring the pressure in said air passage, drive means for moving said valve between a home position and a closing position, and a coupling means for coupling said valve to said drive means, said coupling means being adapted to couple said drive means to said valve after said drive means is brought, in a load-free manner, and without being coupled to said valve, from a rest position into an effectual condition.

2. A device according to claim 1, wherein said coupling means is so designed that the drive means are coupled to the valve only if the energy of that drive means has achieved a predetermined value.

3. A device according to claim 1, wherein said closing means includes a shutter rotatably mounted about a rotational axis.

4. A device according to claim 3, wherein said drive means includes a motor having a drive axis arranged coaxially with said rotational axis of said shutter.

5. A device according to claim 4, wherein said coupling means includes a driving pin on said motor and an eccentric stop face on said shutter, said driving pin and said stop face being adapted to be brought into engagement with one another.

6. A device according to claim 4, wherein said coupling means includes a centrifugal force coupling.

7. A device according to claim 1, wherein said air passage is provided with stops defining said home position and said closing position of said closing means.

8. A device according to claim 3, wherein said shutter is formed elliptically.

* * * * *